(12) United States Patent
Hahami et al.

(10) Patent No.: US 10,488,916 B2
(45) Date of Patent: Nov. 26, 2019

(54) FIBER OPTIC SHAPE SENSING APPLICATIONS

(71) Applicant: DSIT Solutions Ltd., Givat Shmuel (IL)

(72) Inventors: Meir Hahami, Petach Tikva (IL); Itzhak Pomerantz, Kefar Sava (IL)

(73) Assignee: DSIT Solutions Ltd., Givat Shmuel (IL)

( * ) Notice: Subject to any disclaimer, the term of this patent is extended or adjusted under 35 U.S.C. 154(b) by 933 days.

(21) Appl. No.: 14/737,297

(22) Filed: Jun. 11, 2015

(65) Prior Publication Data

US 2015/0359455 A1   Dec. 17, 2015

Related U.S. Application Data

(60) Provisional application No. 62/010,452, filed on Jun. 11, 2014, provisional application No. 62/061,152, filed on Oct. 8, 2014.

(51) Int. Cl.

| | |
|---|---|
| *G06F 3/01* | (2006.01) |
| *G06K 9/00* | (2006.01) |
| *A61B 5/00* | (2006.01) |
| *A61B 5/11* | (2006.01) |
| *A61B 6/12* | (2006.01) |

(52) U.S. Cl.
CPC .............. *G06F 3/011* (2013.01); *A61B 5/112* (2013.01); *A61B 5/6804* (2013.01); *A61B 5/6805* (2013.01); *G06K 9/00342* (2013.01); *A61B 5/6803* (2013.01); *A61B 6/12* (2013.01); *A61B 2562/0266* (2013.01); *A61B 2562/043* (2013.01); *A61B 2562/046* (2013.01)

(58) Field of Classification Search
CPC .......... G06F 3/011; G06F 3/012; G06F 3/014; G06F 3/017; G06K 9/00342; G06K 9/00348; A61B 5/11–113; A61B 5/6801–6829
USPC .......................................... 73/865.4; 600/595
See application file for complete search history.

(56) References Cited

U.S. PATENT DOCUMENTS

| | | | | |
|---|---|---|---|---|
| 5,633,494 | A | * 5/1997 | Danisch ............. | G02B 6/02057 250/227.14 |
| 6,127,672 | A | * 10/2000 | Danisch ................. | G01B 11/18 250/227.14 |
| 6,856,720 | B2 | 2/2005 | Baugh | |
| 8,116,601 | B2 | 2/2012 | Prisco | |

(Continued)

OTHER PUBLICATIONS

Cambridge Consultants, Innovation in wearable tech, https://www.cambridgeconsultants.com/press-releases/innovation-wearable-tech (visited Dec. 12, 2018), Dec. 10, 2014.

*Primary Examiner* — Nathaniel J Kolb
(74) *Attorney, Agent, or Firm* — Roach Brown McCarthy & Gruber, P.C.; Kevin D. McCarthy

(57) ABSTRACT

Using a suitably constructed fiber optic cable and interrogation circuitry, the fiber optic cable can be positioned along an object to monitor its shape and the position of various points along the object thereon. Embodiments disclosed herein apply fiber optic position and shape sensing in various ways. In one embodiment, as subject's gait is monitored for analysis. In another embodiment, a tool is displayed moving within a patient's body. In an additional embodiment, the movement of a subject's head is tracked.

10 Claims, 15 Drawing Sheets

(56) References Cited

U.S. PATENT DOCUMENTS

| | | | |
|---|---|---|---|
| 2002/0040963 A1* | 4/2002 | Clayton | E21B 47/0006 250/227.14 |
| 2006/0013523 A1 | 1/2006 | Childers et al. | |
| 2010/0145235 A1* | 6/2010 | Goldbeck | A61B 5/4561 600/595 |
| 2015/0309563 A1* | 10/2015 | Connor | G06F 3/011 73/865.4 |

* cited by examiner

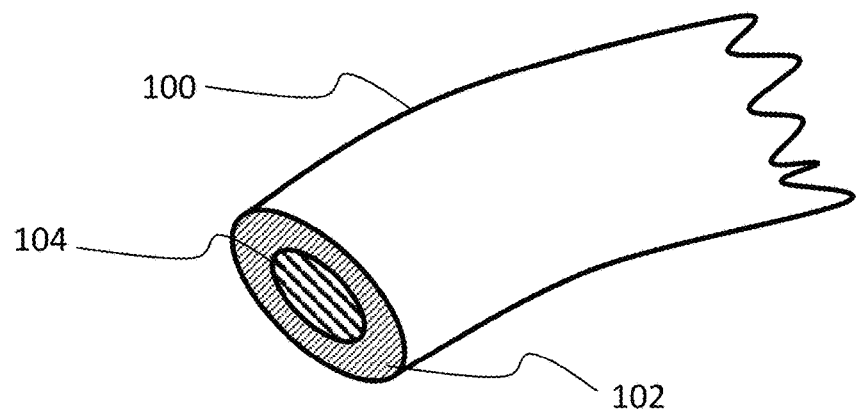
FIG. 1 – PRIOR ART
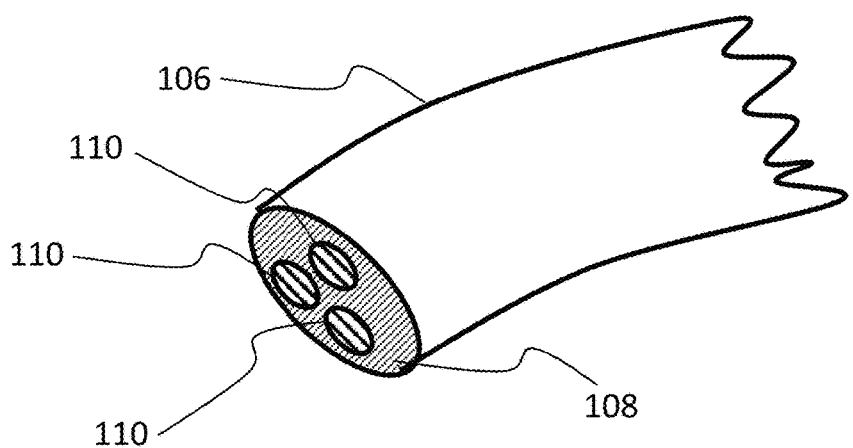
FIG. 2 – PRIOR ART
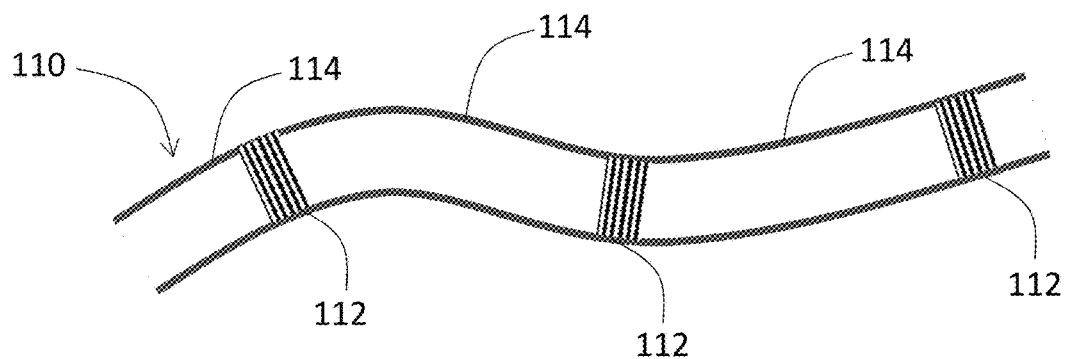
FIG. 3 – PRIOR ART

FIBER OPTIC SHAPE SENSING APPLICATIONS

RELATED APPLICATION

This application claims benefit under 35 U.S.C. § 119(e) of the Jun. 11, 2014 filing of U.S. Provisional Application No. 62/010,452 and the Oct. 8, 2014 filing of U.S. Provisional Application No. 62/061,152, which are hereby incorporated by reference in their entirety.

BACKGROUND

Fiber optic position and shape sensing is known in the art. One example implementation of such technology employs a fiber optic cable installed along a robot appendage to provide the shape and position along the length of the cable and thereby the instantaneous shape of the appendage and spatial coordinates of various points along the appendage.

A prior art example optical fiber 100 has a cladding 102 and a core 104, as illustrated in FIG. 1. The refractive index of the cladding 102 is significantly less than the refractive index of the core 104.

An example optical fiber 106 for fiber optic position and shape sensing has a cladding 108 and three cores 110, as illustrated in FIG. 2. Other example optical fibers for position and shape sensing may have different numbers of cores, the number of cores selected by the engineer according to design requirements and constraints.

FIG. 3 provides a side view of a segment of one of the cores 110 of optical fiber 106. In this implementation of fiber optic position and shape sensing, fiber Bragg gratings 112 are spaced along the core 110 and separated by tethers 114. The fiber Bragg gratings 112 are designed to reflect particular wavelengths of light and to transmit the rest, whereas the tethers 114 transmit all wavelengths.

Interrogation of the fiber Bragg gratings 112 for strain information using known technology provides their spatial coordinates, and the spatial coordinates in turn provide the shape of the optical fiber 106. Non-limiting examples of the technology referenced herein are presented in U.S. Pat. No. 8,116,601 and U.S. Patent Application No. 2006/0013523, both of which are incorporated by reference in their entirety. Using such technology, the spatial coordinates may be determined for a gripper at the end of the robot appendage discussed above, and likewise the shape of the appendage itself may be determined.

However, the full potential of fiber optic position and shape sensing has yet to be fully exploited.

SUMMARY

Embodiments of the present invention employ fiber optic position and shape sensing for various purposes, including gait monitoring, catheterization, and head movement tracking.

The invention may be embodied as a garment having fabric and at least one shape sensing optical fiber. The fabric is sized and shaped to envelope at least a portion of a wearer's body. The at least one shape sensing optical fiber is connected to the fabric such that a portion of the optical fiber extends along the fabric to indicate the shape of the fabric.

The invention may also be embodied as a method of the monitoring gait of a subject. The garment described in the preceding paragraph is provided to the subject. The at least optical fiber is interrogated to obtain coordinates along the optical fiber(s). This interrogation is repeated to obtain coordinates along the at least one optical fiber at multiple instants in time.

The invention may further be embodied as system for displaying a tool moving within a body. The system includes an X-ray machine, a shape sensing device, an image synthesizer, and an image integrator. The X-ray machine generates for a portion of the body (1) a first set of architecture images indicating the locations of internal body parts, and (2) a first additional architecture image indicating the location of the tool. A shape sensing device generates for the body portion a first set of envelope images and an additional envelope image, the envelope images indicating the size and shape of the body portion. An image synthesizer generates a second additional architecture image using the first set of envelope images, the first set of architecture images, and the additional envelope image, the second additional architecture image indicating the location of the internal body parts surrounding the tools. The image integrator superimposes for display one of the first and second additional architecture images on the other to show both the tool and the surrounding body parts.

The invention may additionally be embodied as a method of displaying a tool moving within a body. The method includes, during a first time period: obtaining a first set of envelope images of a portion of the body, the first set of envelope images providing data indicating the size and shape of the body portion; and obtaining a first set of architecture images of the body portion, the first set of architecture images providing data indicating the locations of internal body parts. The method further includes, during a second time period: obtaining an additional envelope image, the additional envelope image providing data indicating the size and shape of the body portion; obtaining a first additional architecture image, the first additional architecture image indicating the location of the tool; using the first set of envelope images, the first set of architecture images, and the additional envelope image to synthesize a second additional architecture image, the second additional architecture image indicating the location of the surrounding internal body parts; and displaying one of the first and second additional architecture images superimposed on the other to show both the tool and the surrounding body parts.

The invention may also be embodied as a device for tracing motion of a first object relative to a second object. The device has first and second shape sensing fibers. The first shape sensing fiber is mechanically linked to the first object at a first point. The second shape sensing fiber is mechanically linked to the first object at a second point, which is spaced apart from the first point. Both the first and the second shape sensing fibers are configured for mechanical linkage to the second object.

Embodiments of the present invention are described in detail below with reference to the accompanying drawings, which are briefly described as follows:

BRIEF DESCRIPTION OF THE DRAWINGS

The invention is described below in the appended claims, which are read in view of the accompanying description including the following drawings, wherein:

FIG. 1 illustrates a prior art optical fiber;

FIG. 2 illustrates a prior art optical fiber having three cores;

FIG. 3 illustrates a core of a prior art optical fiber having fiber Bragg gratings spaced along the core;

DETAILED DESCRIPTION

The invention summarized above and defined by the claims below will be better understood by referring to the present detailed description of embodiments of the invention. This description is not intended to limit the scope of claims but instead to provide examples of the invention. Described herein are example embodiments of the present invention employing fiber optic position and shape sensing for various purposes.

The present inventors realized that fiber optic position and shape sensing, when implemented correctly, can be employed to facilitate gait analysis. Gait analysis in this context references the systematic study of animal/human locomotion, or more specifically the study of human motion, using the eyes and the brains of observers, augmented by instrumentation for measuring body movements, body mechanics, and the activities of the muscles. Gait analysis is used to assess and treat individuals with conditions affecting their ability to walk. It is also commonly used in sports biomechanics to help athletes run more efficiently and to identify posture-related or movement-related problems injured persons.

When attempting to diagnose the medical conditions of patients with walking problems, it is very valuable to have a gait monitoring system that the patients may operate when not in a medical clinic and while they perform their life routine. Two reasons for this are that (1) the problems are often incidental, and days or weeks can pass between incidents and that (2) the problems are often related to walking surface textures and slopes, which are not simulated sufficiently, if at all, in the clinic.

The present inventors realized that fiber optic position and shape sensing can be exploited to improve upon known gait analyses techniques, as it is not overly heavy or cumbersome, when implemented as disclosed herein, and it can easily monitor more points along a patient's body. In addition to gait analysis for purposes of medical treatments, embodiments of the present invention may be implemented for analyses within the realms of sports, physiotherapy, acrobatics, biological research, occupational therapy, and other physical activities in which it is desired to measure and record the motion of human limbs.

Fiber optic cable with a large number of fiber Bragg gratings spaced close together enable more accurate shape and position sensing. Prior art systems, which may be in the same field of endeavor as the presently disclosed embodiments, cannot provide as accurate data when only measuring the position of a few points.

Figure 4:
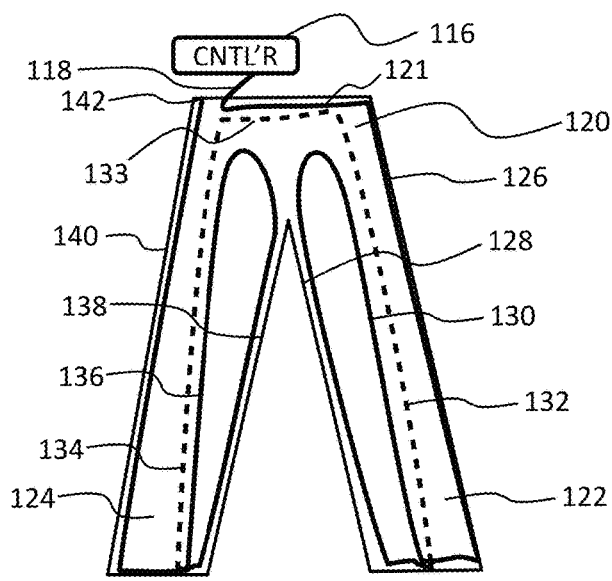
FIG. 4 provides a front view of an embodiment of an optical fiber extending along a pair of trousers to provide shape information about the wearer's body.

Reference is made to the embodiment of the invention illustrated in FIG. 4, in which an optical fiber extends along a garment to provide shape information about the wearer's body.

A portable shape sensing fiber controller 116, such as one available from Fraunhofer Institute, is worn on a belt (not shown) of a patient and powered by batteries. An optical fiber 118 engaged with the controller 116 is threaded through, sewn to, or otherwise engaged to a pair of trousers 120 and initially extends to one of the sides of the trousers 120. See fiber segment 121. The optical fiber 118 then extends down and up each of the two trouser legs 122, 124 twice in a path along each leg 122, 124 in front, in back, on the inner side (inseam), and on the outer side. In FIG. 4, the view facing the front side of the trousers 120, the optical fiber path, after it begins at the controller 116 and extends horizontally at the fiber segment 121, leads down the left leg's external side 126 (opposite the inseam), up the left leg's interior side 128 (inseam), down on the left leg's front side 130, and up the left leg's rear side 132, horizontally at fiber segment 133 to the right leg 124, then down the right leg's rear side 134, up the right leg's front side 136, down the right leg's interior side (inseam) 138, and finally up the right leg's external side (opposite the inseam) 140 so the distal end 142 is positioned in the region of the wearer's belt. The optical fiber 118 in this embodiment may have a radius of curvature of only a few centimeters enabling U-turns thereof at the ends of the trouser legs 122, 124.

The optical fiber 118 as a single unit provides raw data to the controller 116 thereby enabling the controller 116 to calculate the pattern on (shape of) the fiber in space relative to the controller 116. As the controller 116 is essentially fixed to the belt of the trousers 120 in operation, the information about the shape of the optical fiber 118 is easily expressed in a reference frame relative to the body of the patient.

The controller may interrogate the shape sensing fiber, the optical fiber 118, at sampling rates of hundreds of times per second, so the position of each fiber Bragg grating along the optical fiber 118 can be determined often enough to provide a very detailed record of the motion of the legs within the trouser legs 122, 124. Because the optical fiber extends along four sides of each leg (front, back, inside, outside), general cross sections along each leg can be monitored.

Figure 5:
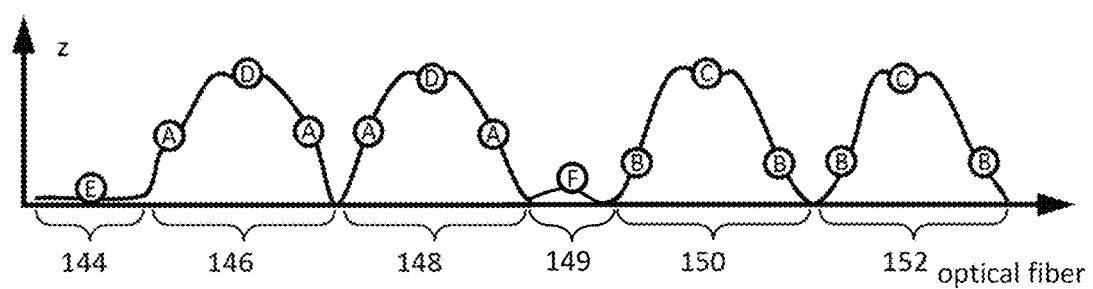
FIG. 5 presents a plot providing at an instant in time a spatial coordinate of a point along the optical fiber of FIG. 4 as a function of the point's position along the length of the optical fiber.

FIG. 5 presents a plot providing at an instant in time the vertical coordinate (z) of a point along the optical fiber 118 measured down from the controller 116 as a function of the point's position along the length of the optical fiber 118. Analogous charts for two horizontal coordinates (x, y) may also be provided.

Reference numbers 144-152 indicate regions of the optical fiber 118 which extend along the trousers 120 horizontally or down/up a leg as follows: Region 144 indicates the segment 121 of the optical fiber 118 extending along the belt area of the trousers 120 from the controller 116. Region 146 indicates the segment of the optical fiber 118 extending along the left leg 122 down the exterior side 126 and then up the interior side 128. Region 148 indicates the segment of the optical fiber 118 extending along the left leg 122 down the front 130 and up the back 132. Region 149 indicates the segment 133 of the optical fiber 118 extending horizontally to the right leg 124 along the rear side of the trousers 120. Region 150 indicates the segment of the optical fiber 118 extending along right leg 124 down the back 134 and up the front 136. Finally, region 152 indicates the segment of the optical fiber 118 extending along right leg 124 down the interior side 138 and up the exterior side 140.

Various points along the plot of FIG. 5 are marked with reference signs A-F, which correspond to parts of the wearer's body. The reference sign A indicates the location of the wearer's left knee. The reference sign B indicates the location of the wearer's right hip. The reference sign C indicates the location of the wearer's right foot. The reference sign D indicates the location of the wearer's left foot. The reference sign E indicates the location of the wearer's navel or slightly below the navel, depending on the style of the trousers 120. The reference sign F indicates the location of the wearer's lower back/upper posterior.

The plot of FIG. 5 provides for a specific instant in time and at any point along the optical fiber 118 the vertical (Z) coordinate of the body part contacting the point along the optical fiber 118. With analogous charts for the two horizontal coordinates (X,Y), the spatial coordinates of the body part at a given instant in time may be determined and recorded.

Figure 6:
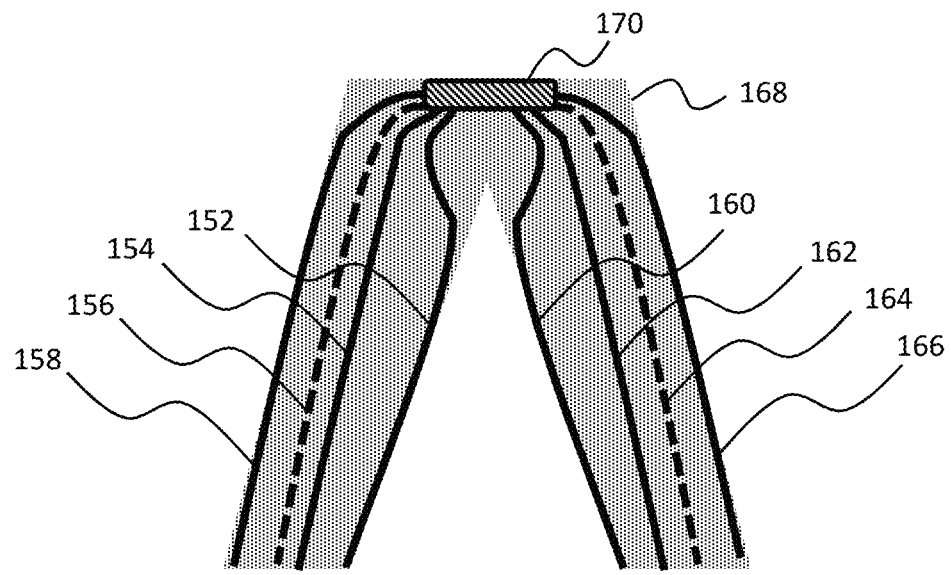
FIG. 6 provides a front view of an alternate embodiment of the invention in which multiple optical fibers extend along a pair of trousers.

An alternate embodiment is illustrated in FIG. 6. In contrast to the embodiment of FIGS. 4 and 5, which may be implemented so that the optical fiber 118 curves in the form of a "U-turns" having small radii at the end of the trouser legs 122, 124, the present embodiment reduces the potential distortion of the shape of the trousers and any associated discomfort or inconvenience that may result from the rigidity of a fiber's protective shell in the region of the U-turn.

The embodiment of FIG. 6 requires no U-turns of a fiber. Instead, eight strips of fiber 152-166 extend along a pair of trousers 168 from a common eight-port optical switch 170, such as the switch described in U.S. Pat. No. 6,856,720, herein incorporated by reference. The switch 170 can be embedded in the controller (not shown) at the belt (not shown) of the trousers 168. The optical switch 170 is configured to successively select one of the eight fiber strips 152-166 and to operatively connect the selected strip to the controller for shape sensing. As the fiber strip in operation can be switched at a rate of few hundred times per second, the controller has access to each of the fiber strips 152-166 at a sufficient sampling rate. The eight fiber strips 152-166 cover the same areas of the trousers as in the embodiment of FIGS. 4 and 5.

The fabric used in embodiments of garments described herein may be cloth, mesh, or even rubber (as in a SCUBA wetsuit), as non-limiting examples. As in the embodiments presented above, the fabric that is sized and shaped to envelope at least a portion of the wearer's body below the waist. Moderately loose trousers may be tolerated for some circumstances, but in other circumstances snug-fitting tight-like garments, and as shown above, even garments enveloping the subject's feet, are preferable.

The optical fibers in garments discussed herein may be connected to the fabric in multiple ways, such by adhesive or by being threaded into the fabric, so that they extend along the fabric to generally match the contour of the user's body. The optical fibers may lie within the garment and even contact the wearer, they may lie outside the fabric, or even be imbedded and unseen within the fabric. The fibers can cross each other and slightly press on each other, thus creating pairs of points of stress at different points along the fiber, but with identical XYZ coordinates. Such pairs can be used for calibration of the sensed position of the fibers, forcing their position to be the same, and interpolating between them to calibrate other points along the fiber.

One embodiment of interpreting the fiber coordinates, such as those obtained using the trousers of FIG. 4 or 6, is discussed with reference to FIGS. 7A and 7B.

Figure 7A:
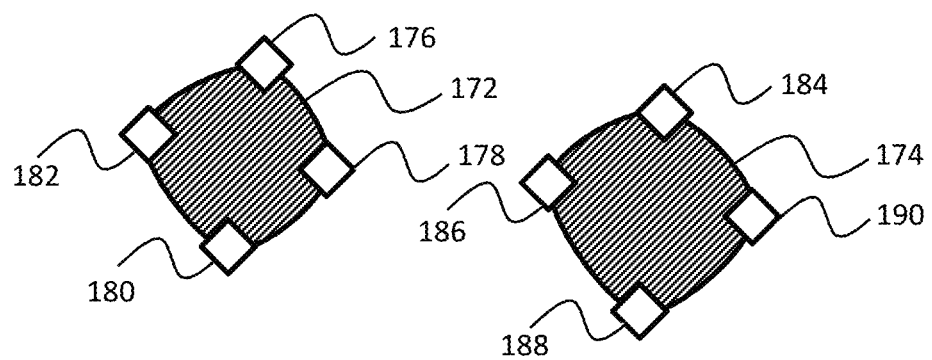
FIGS. 7A and 7B illustrate cross sections of a person's legs under differing circumstances and the locations thereon of points of the optical fiber(s)
Figure 7B:
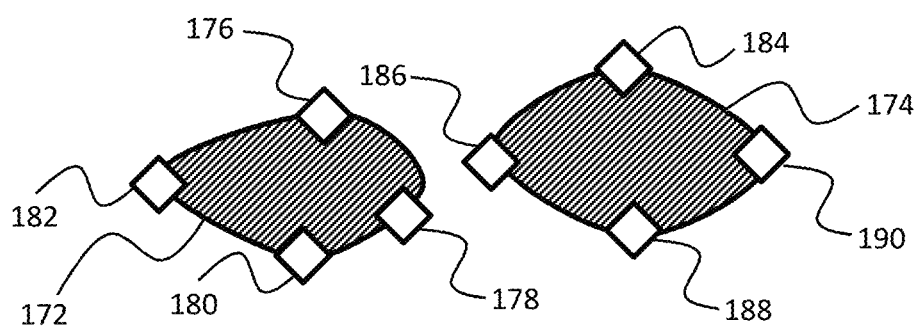

FIG. 7A provides an illustration of an approximate cross section of the left leg 172 and the right leg 174 at one elevation (z-coordinate) along the leg. The trousers in this embodiment fit the wearer snugly, such as is the case with long underwear or tights. Such trousers are useful when the actual cross section of the flesh of the leg is of interest. In medical applications, the cross section of the legs may indicate pressure applied to the leg by sitting or by leaning against hard surfaces. In sports applications, the cross section of the legs may indicate the volume of the muscle at every point along the leg and at any given instant in time. The cross section perimeter includes the points in contact with the optical fiber(s), as discussed above. Points 176, 178, 180, and 182 on the left leg 172 are the front, inside, back, and outside points of the left leg cross section, and points 184, 186, 188, and 190 on the right leg 174 are the front, inside, back, and outside point of the right leg cross section FIG. 7B provides an illustration of the cross section of the same legs 172, 174 at the same elevation but under different conditions. The coordinates of the cross section perimeters in FIGS. 7A and 7B, other than for the eight points marked in the figures, are approximate, because it is not necessary to know all the perimeter coordinates precisely. Because the front and back points of each of the legs 172, 174 are closer together in FIG. 7B than in FIG. 7A, and because the inside and outside points of each of the legs 172, 174 are farther apart in FIG. 7B than in FIG. 7A, it can be deduced that the cross section is more elliptical in FIG. 7B than in FIG. 7A, so the legs may be under compression or the wearer of the trousers is sitting.

The cross section of a subject's legs that is of interest in this embodiments is generally parallel to the subject's waist when he/she stands. When he/she walks, though, that same cross section is not parallel to the subject's waist, as the legs are not perpendicular to the ground most of the time. Such does not present a problem in obtaining cross section data at different points of the subject's stride, because the four points of the optical fiber in a cross section plane do not change just because the plane is not parallel to the subject's waist.

Figure 8:
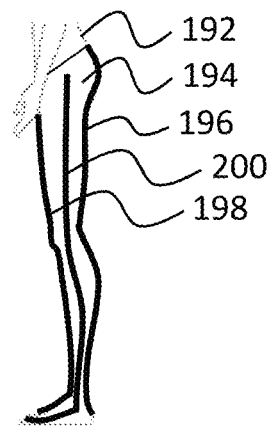
FIG. 8 illustrates the invention embodied as a garment that envelopes also the wearer's feet and provide position and shape information thereof.

The embodiment of FIG. 8 enables determination and recordation of body coordinates down to the end of the foot, which is useful in certain gait analysis. Instead of using trousers that barely extend below the wearer's ankles, tights enveloping even the entire feet are implemented. The optical fibers connected to the tights extend to the feet on the right, left, and top sides. The embodiment can even be constructed so that the fibers extend to the toes. The back optical fibers, which would have extended under the feet if implemented to reach the toes, may be trimmed at the heel to avoid the inconvenience or discomfort to the patient that may have been caused by stepping on the optical fibers. FIG. 8 shows a patient 192 wearing tights 194 with three of the eight optical fiber strips visible, front left optical fiber 196, rear left optical fiber 198, and left exterior optical fiber 200.

Figure 9:
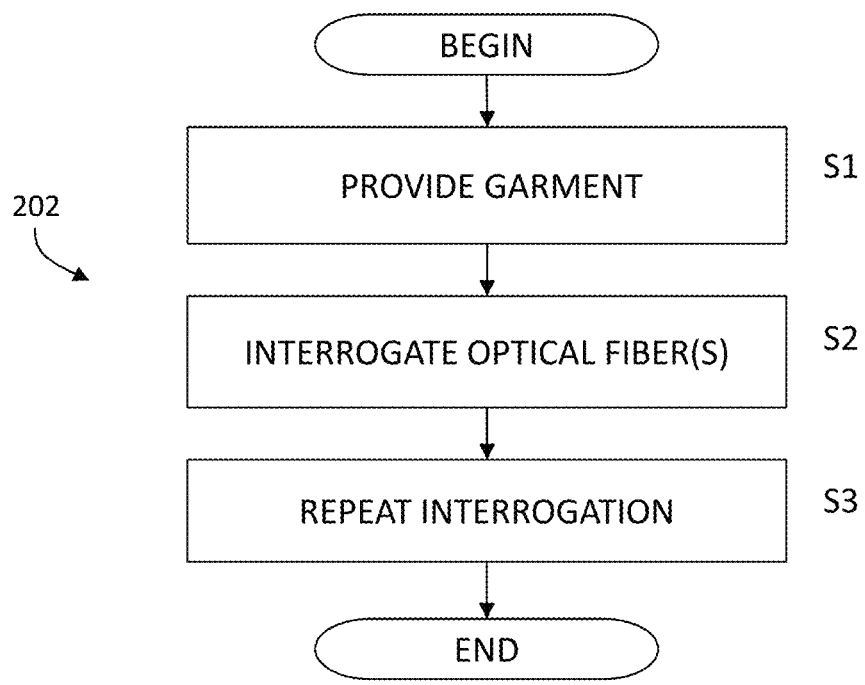
FIG. 9 presents a flowchart illustrating the invention embodied as a method of monitoring the gait of a subject.

The invention may also be embodied as a method of monitoring the gait of a subject. The subject may be a patient for whom medical care providers must observe the patient's gait in order to administer proper treatment therefor. Alternatively, the subject may be an athlete who desires to improve his/her sports performance, as another non-limiting example. This method is described with reference to the flowchart 202 in FIG. 9.

The method begins providing the subject with the garment such as the trousers or tights of the embodiments described above. (Step S1.) The garment has fabric that is sized and shaped to envelope at least a portion of the subject's body below the waist. The fabric may be cloth, mesh, or even rubber, as non-limiting examples. Moderately loose trousers may be tolerated for some circumstances. In other circumstances, though, snug-fitting tight-like garment, even those enveloping the subject's feet, are preferable. As in the embodiments described above, one or more optical fibers are connected to the fabric to enable fiber optic position and shape sensing.

The next step is to interrogate the optical fiber(s) to obtain coordinates along the optical fiber(s). (Step S2.) If it is desired to monitor changes in cross section of the subject's legs, the coordinates are obtained for a set of points along the optical fiber(s) that for one instant in time lied in a plane parallel to the subject's waist and intersecting the subject's legs.

The optical fiber(s) is interrogated again to obtain coordinates along the optical fiber(s) at multiple instants in time. (Step S3.) When it is desired to monitor changes in the cross sections of the subject's legs, the repeated interrogation provides the coordinates of the set of points that once lied in the same plane as discussed in the preceding paragraph (which may later lie in a different plane according to the instantaneous position and shape of the subject's legs) to enable monitoring of the changes in the cross sections of the subject's legs.

In another embodiment, the trajectory of the optical fibers a garment make the cross section determination more accurate by coiling the fibers around the leg portion of the garment in a helical pattern, thus making points of physical proximity be also close along the fiber length. The optical fiber interrogation may be repeated many times to provide data indicative of the changing shape of the subject's lower body, which enables gait monitoring.

The present inventors also realized that fiber optic position and shape sensing, when implemented correctly, can be employed to reduce health risks to the medical staff and to the patient during catheterization procedures. Catheterization is a well-known medical procedure by which diagnosis or treatment within a body vessel, such as a blood vessel or the digestive track, is provided using a tool, such as a catheter, that travels through the vessel and is operated from outside the patient's body. The tool can be inserted into the vessel from its end (an orifice) or through an incision in the patient's body.

In order to operate the tool at the end of the catheter, the operator normally needs to "see" (image) the tool and the associated region of the body. As one example, real time X-ray radiation is used to image the tool and the body region, and the operator performs the procedure while observing the imaging screen.

In order to make the vessel visible in the X-ray image, the vessel needs to be contrasted against the rest of the patient's body, and in many cases such is achieved by injecting a radiation absorbent fluid into the vessel. While the contrasting fluid is present in the vessel, the vessel image is darker than the image of the rest of the body, but the vessel image is not as dark as the image of the metal tool. Accordingly, the operator obtains a clear image of the tool, on the background of a lighter image of the vessels, on a still lighter image of the soft tissues.

Unfortunately, imaging the medical procedure as described has the following two disadvantages: For procedures in which the vessel is a blood vessel, the contrasting fluid tends to accumulate in the kidneys and eventually damage them. Also, over time the operation team and the patient are exposed to excessive X-ray radiation.

The present inventors realized that fiber optic position and shape sensing can be exploited to reduce the needed amounts of both the contrasting fluid and X-ray radiation. The result is that both patients and health care personnel are exposed to fewer health risks. Further, minimal additional equipment is needed to upgrade to embodiments of the present invention. That is, embodiments of the invention use much of the same equipment that typically is already in use.

In one embodiment, the patient wears tight clothing stretched over part of the body. The type of the clothing item is determined according to the part of the body that is the subject of the medical procedure. For example, for a chest or a stomach operation, the clothing item/garment resembles a short-sleeve shirt. As another example, for a foot or a leg operation, the garment resembles a sock or tight trousers.

In an embodiment, the clothing item is configured to capture an accurate, real-time, three-dimensional map of a clothing item's shape in space, and that shape is indicative of the body shape enveloped by the clothing item.

Embodiments rely on an assumption that, when a semi fluid body, such as the human body, is distorted by external or internal forces, its internal architecture (location and shape of internal organs) distorts essentially elastically. That is, if at one instant in time the internal and external forces on and in the body cause it to have an outer envelope E and an internal architecture A, then at a different instant in time (sufficiently close to the first instant so that none of the internal organs have changed its shape) the very same set of internal and external forces are applied, the body will return to the same outer envelope E and the same internal architecture A.

This assumption can easily be proven and demonstrated for a one dimensional system, which models the body as a set of weights and springs, as illustrated in FIGS. 10A-10D (discussed in more detail below), and can also be demonstrated in a two dimensional system (also discussed below), where the body has a surface resembling an elastic (not necessarily uniform) sheet, and it is as intuitive and demonstrable to apply it in a three-dimensional set up, whether discrete (a set of weights inter connected by springs) or continuous.

Following this assumption, and as both the envelope model and the internal architecture of the human body are complex, the following assumption is also made: there is a very high correlation between the shape of the envelope E and the internal architecture A. Accordingly, without any knowledge of the internal and external force distribution in and on the body, the architecture of internal organs at time $T_1$ can be estimated if given the following: (1) the envelope pattern $E_0$ of the body at time $T_0$, with $T_0$ being near $T_1$; (2) the architecture $A_0$ of the body at time $T_0$; (3) the envelope $E_1$ of the body at time $T_1$, and (4) $E_0$ being equal to $E_1$. With this information and under those conditions, it is assumed that $A_1=A_0$. In other words, if at two points in time close together the body envelope is the same, then the body internal architecture is the same.

Under the preceding assumption, one catheterization process embodying the present invention has two parts: a training session and an operation session. Each part is elaborated upon as follows:

During the training session, the patient rests on an operating table or like platform wearing tight clothing to map the body envelope. The operational arena, the segment of the body that is of interest, is imaged using ordinary X-ray imaging. Contrasting fluid is injected into the patient's vessels. X-ray images are continuously recorded, as well as the body envelope pattern. The operation team does not need to be present in the operation room during the training session, as no operation is being performed. Thus, the operation team is not exposed to the radiation. The length of time for the training session need only be long enough to encompass three to four breathing cycles and ten to twenty heart beat cycles. If the contrasting fluid is expected to fade before the training session end, additional contrasting fluid may be administered automatically so that the vessels retain a good visual contrast throughout the training without requiring the presence of the medical staff. Additional information that may be useful to determine the respiration cycle and the heart cycle may also recorded during the training session.

At the end of the training session, the radiation is turned off, and the contrasting fluid is no longer administered. The system is now ready for the operation. The accumulated training data, typically several hundred envelope and architecture images, are stored.

During the operation session, the X-ray radiation is turned on at a very weak power that hardly endangers the team and the patient. This power is strong enough to show the metal catheter body on the background of the live tissues of the body, but is too weak to show any distinction between organs.

The system, however, continues to obtain envelope data from the clothing. For each capture of the envelope $E_n$, the system searches for the image from the training session that is most similar to $E_n$. This can be done analytically and empirically, both of which are discussed below. Once the most similar envelope has been detected, the corresponding architecture $A_n$ is retrieved and is displayed on the X-ray screen, superimposed on the real time image of the catheter.

As can be appreciated, this image is very rich with contrasting fluid, and the internal organs, such as vessels, are displayed in their real position or very near to it. This provides to the operator a map of the vessel that is good enough to enable him direct the catheter safely to its destination.

If the patient moves, the correlation between the envelope E and architecture A is lost, and the training database cannot be relied upon. When this happens, the system alerts the operator (as the clothing reports such motion in real time), and a new training session is then conducted.

One empirical method of finding the training envelope that is most similar to the real time envelope is based on finding the minimal distance between two surfaces. Two example methods are as follows:

The first method is to estimate the distance between an envelope $E_1$ and an envelope $E_2$ is based on the volume of space captured between the $E_1$ and $E_2$. This volume is zero, if the two envelopes are identical. The volume increases as the distance between $E_1$ and $E_2$ increases.

A second method of determining the distance between the two envelopes $E_1$ and $E_2$ is to calculate the RMS distance between control points on the envelopes. The term "control point" is used here in the mathematical sense as explained in http://en.wikipedia.org/wiki/Control_point_(mathematics). It is a set of points in space that define a shape of a surface, and can be considered as "samples" of the surface. If we use a shape sensing fiber for determining the envelope of the clothing that that the patient wears, then a set of points at predetermined distances along the fiber from its entrance can serve as control points, because, when the envelope at two times are similar to each other, these control points will be close to each other and the RMS distance between them will be very small.

The empirical method of finding the relevant point of the training set works well when the training set is rich and there is a high probability that every shape of the envelope determined during operation replicates a shape that was captured in the training. This will happen when the training session is long and covers all possible combinations between causes of distortion (i.e. respiration and heart bit).

However, embodiments of the present invention also cater to situations where it is not as likely to find in the database of envelopes acquired during training a good enough replication of some shapes that happen during operation. In such cases, the following analytical process may be used.

This analytical process assumes that there are two periodic causes for the changes in the shape of the body. Those causes are respiration and heart pulsation, and they are referenced below using "R" and "H," respectively. The analytical process begins as follows:

A relatively large set of control points is set.

An average static position of the body (a rest envelope) is determined by averaging data obtained during the training session. The average static position is used as a reference so that the positions of individual control points can be described as vectorial deviations from the rest envelope.

The control points are monitored and recorded during the training session.

The effect of the first cause of motion (R) on each control point is isolated from the effect of the second cause of motion (H) as follows:

The cycle of the R motion is broken into a number of phases. Typically, eight phases are chosen, each phase encompassing 45 degrees of a 360 degree cycle.

A detectable event in the R cycle is selected as trigger. This can be a distinct point on the cardiogram. (The trigger event preferably is taken from a different physiological source, such as respiration air flow).

The position of each control point (as a vectorial deviation from the rest envelope) at each of the eight R phases is averaged over all the H cycles in the training session. The effect of the H cause is averaged out as noise.

The result is the contribution of the R cause to the position of each control point.

Then the effect of the H cause on the motion of every control point is determined as follows:

The cycle of the H motion is broken into a number of sections. Typically, eight phases are chosen, each encompassing 45 degrees of a 360 degree cycle.

A detectable event, such as the transition from exhaling to inhaling in the breathing cycle, in the H cycle is selected as a trigger. (The trigger event preferably is taken from a different physiological source, such as the ECG).

The position of each control point (as a vectorial deviation from the rest envelope) at each of the eight H phases is averaged over all the R cycles in the training session. The effect of the R cause is averaged out as noise.

The training session is now over, and the operation session begins.

During the operation session, the R trigger and the H trigger are monitored, and the H phase (one of eight) and the R phase (one of eight) are determined The contribution of the R cause and the H cause are retrieved from the training database, and are vectorially summed to estimate the dislocation of each control point from the rest envelope due to the joint effect of the H and R causes in their current phase.

Then the system takes the rest envelope and moves all the control points to their currently calculated position, providing the estimated current envelope ($E_s$). This calculation replaces the selection of one envelope from the training set, as it is expected at times that that there is no envelope in the training set that is similar enough to the current envelope.

Because the envelope of the body is synthetic and there is no corresponding training architecture, the system needs to synthesize the architecture ($A_s$) to be displayed. The architecture associated with the envelope from the training session that is most similar to the current envelope ($E_r$) is selected as a reference architecture ($A_r$) using the same process described above as the empirical method. A graphical procedure known as "rubber sheeting" is applied in three dimensions to the reference architecture $A_r$ to produce the synthetic architecture ($A_s$) and the synthetic architecture $A_s$ is displayed.

In one embodiment, one of the two (empirical and analytical) methods is used to synthesize an approximation of the architecture of the body of a patient at real time, based on the current envelope shape of the body or the current phase in the cyclic motion of the body.

In another embodiment, small errors in the synthesis of the architecture can be corrected by rubber-sheeting the local architecture so the apparent trajectory of a main vessel is aligned with the trajectory of the catheter if the two trajectories are evidently associated. The process of rubber sheeting is known the art, as evident from U.S. Pat. No. 5,491,563, incorporated by reference herein.

The capturing of the shape of the envelope and the capturing of the phase in the periodic cycle of the body are both referred to as "capturing an index" to the shape of the envelope, as by using these parameters as indexes to the database, one can retrieve an approximation of the shape of the body using the empirical or the analytical methods described above.

As also discussed above, embodiments described herein rely on the assumption that, when a semi fluid body (for example, the human body) is distorted by external or internal forces, its internal architecture (location and shape of internal organs) distorts elastically. Thus, if at one instant in time the internal and external forces on and in the body cause it to have an outer envelope E and an internal architecture A, then at a different instant in time (sufficiently close to the first instant so that none of the internal organs have changed its shape) the very same set of internal and external forces will be applied, the body will return to the same outer envelope E and the same internal architecture A. This principle is discussed with reference to FIGS. 10A-10D and 11.

Figure 10A:
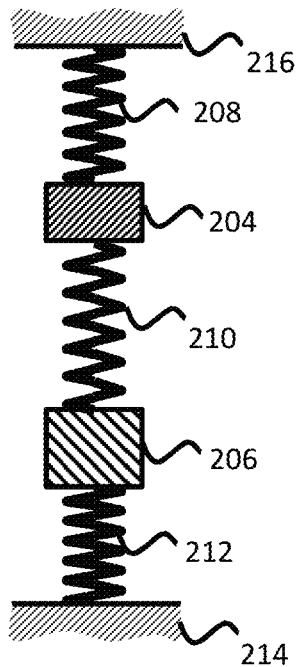
FIGS. 10A-10D illustrate a relationship between internal and external forces and an "envelope" bounding a one-dimensional "semi-rigid" system.

FIGS. 10A-10D illustrate in one dimensional the correlation of the internal architecture with the external envelope. In FIG. 10A, a linear structure of two solid objects 204 and 206 and three springs 208, 210, and 212 is suspended in stable equilibrium between a floor 214 and a ceiling 216.

Figure 10B:
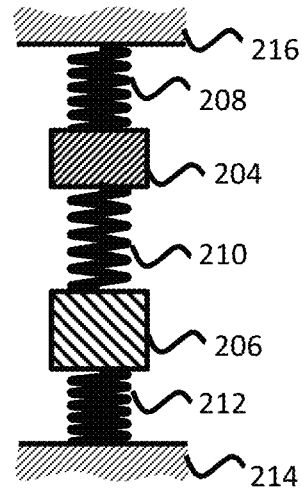

In FIG. 10B, the ceiling 216 is lowered. As a result, the springs change their length and a new state of equilibrium is achieved, where objects 204 and 206 assume new positions, still suspended by the three springs 208, 210, and 212.

Figure 10C:
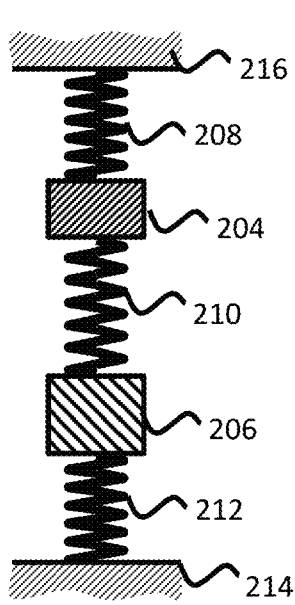

In FIG. 10C, the ceiling 216 is raised to a new position. As a result, the springs 208, 210, and 212 change their length and a new state of equilibrium is achieved, where objects 204 and 206 assume another new positions, still suspended by the three springs 208, 210, and 212. In all three configurations of FIGS. 10A, 10B, and 10C, the ceiling 216 and the objects are in different positions.

Figure 10D:
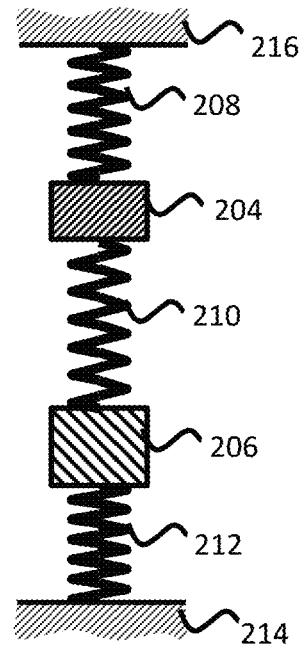

In FIG. 10D, the ceiling 216 is returned to the original height of FIG. 10A. It is evident that in the steady state (following the transients of motion) the whole configuration will resume the state of FIG. 10A, as in case one of the objects will not be in its original state, the balance of the forces on it will not be zero and it will move. If for example object 204 will be higher than it was in FIG. 10A, the pulling force of spring 208 will be lower than it was originally, and the pulling force of spring 210 will be higher than it was originally, and the forces of the springs 208, 210, and 212 and gravity will not be balanced.

Based on the discussion above, one may conclude that in one dimension, there is a 1-to-1 relationship between the position of the ceiling (the envelope) and the position of the objects (the architecture).

Figure 11:
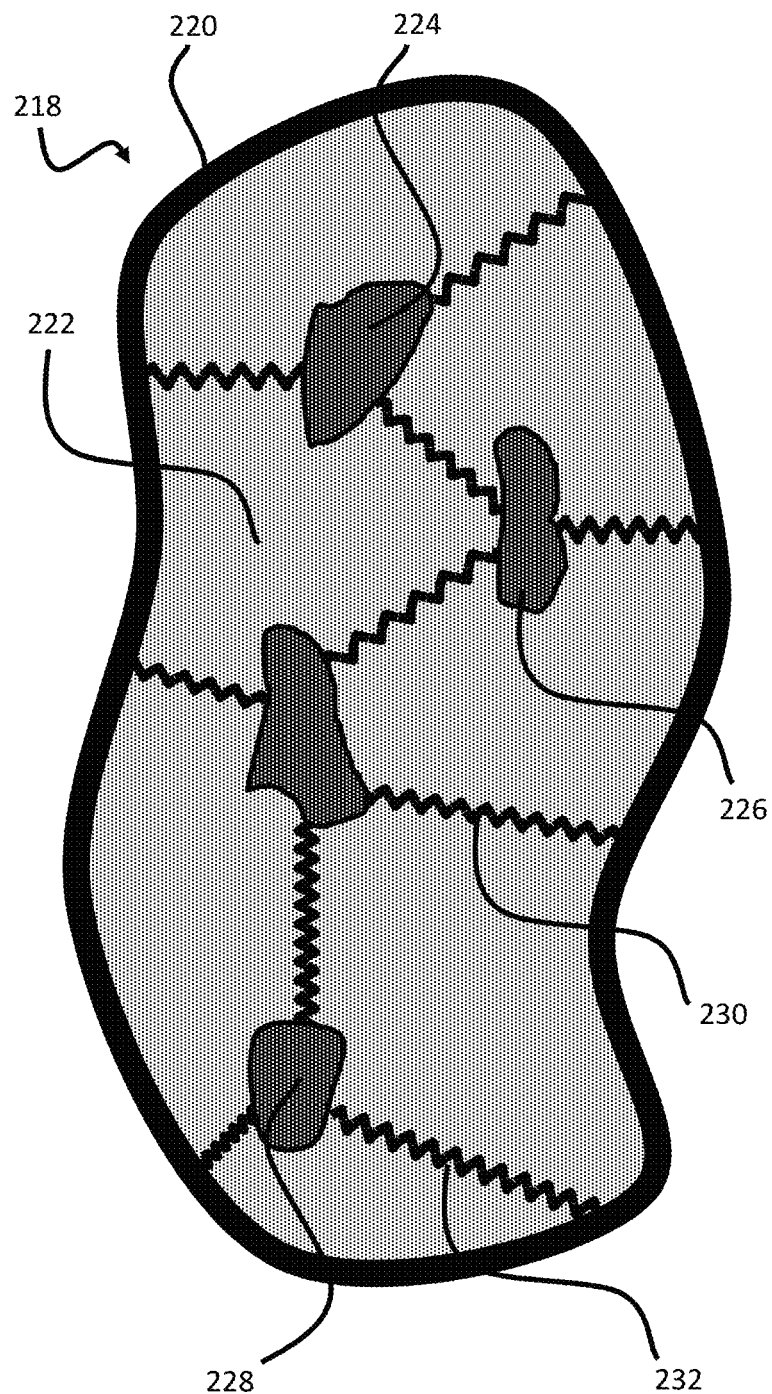
FIG. 11 illustrates a relationship between internal and external forces and an envelope bounding a two-dimensional semi-rigid system.

Reference is now made to FIG. 11, which illustrates a two-dimensional object 218 having a skin 220 and an internal architecture 222. Solid objects, such as objects 224, 226, and 228 are suspended by elastic members such as 230 and 232 from the skin 220 of the body.

This illustrates the extension of the one-dimensional assumption illustrated in FIGS. 10A-10D to two dimensions. The present assumption is that, in a two-dimensional body containing solid objects suspended by elastic members, if the body is slightly distorted by forces, and then returned to its original envelope, the suspended items will resume their position within the original architecture. Any deviation of any of the objects from their original positions will cause them to depart from equilibrium.

Figures 12A, 12B:
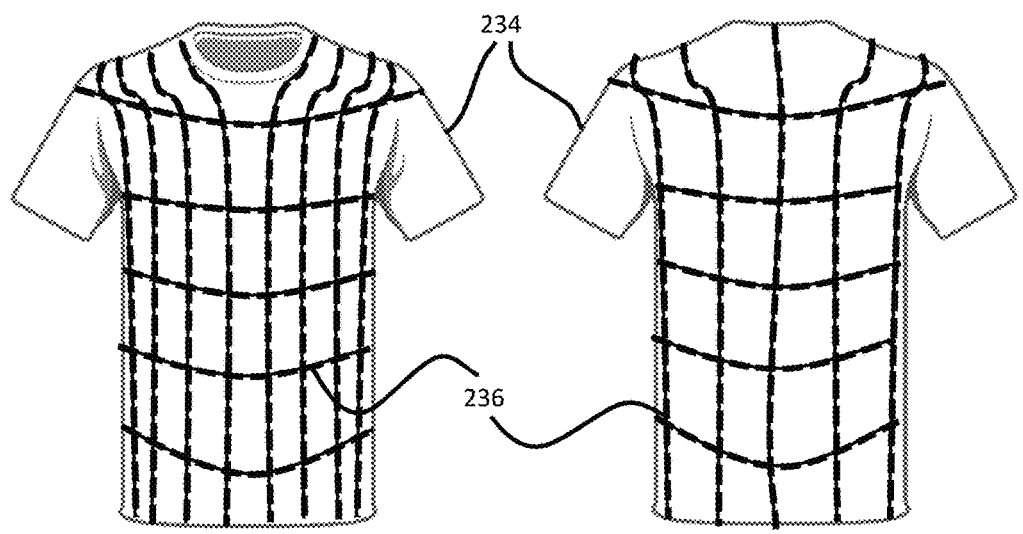
FIGS. 12A and 12B illustrate front and rear views, respectively, of snug-fitting garment monitoring the envelope of a three-dimensional system, a human torso, in accordance with an embodiment of the invention.

Reference is now made to FIGS. 12A and 12B, which illustrate front and rear views, respectively, of an elastic (snug-fitting) T-shirt 234 in which are weaved one or more shape sensing fibers 236 in a grid. An example grid size for this embodiment is 5×5 cm². The shape sensing fiber(s) are interrogated by an electronic interrogator such as that available from Fraunhofer Institute (mentioned above) and provide a real time map of the envelope of the body that wears it. Alternatively, known methods of digitization of envelopes of three-dimensional bodies may be used, such as using three-dimensional scanners, as described in http://en.wikipedia.org/wiki/3D_scanner.

Figures 13A, 13B:
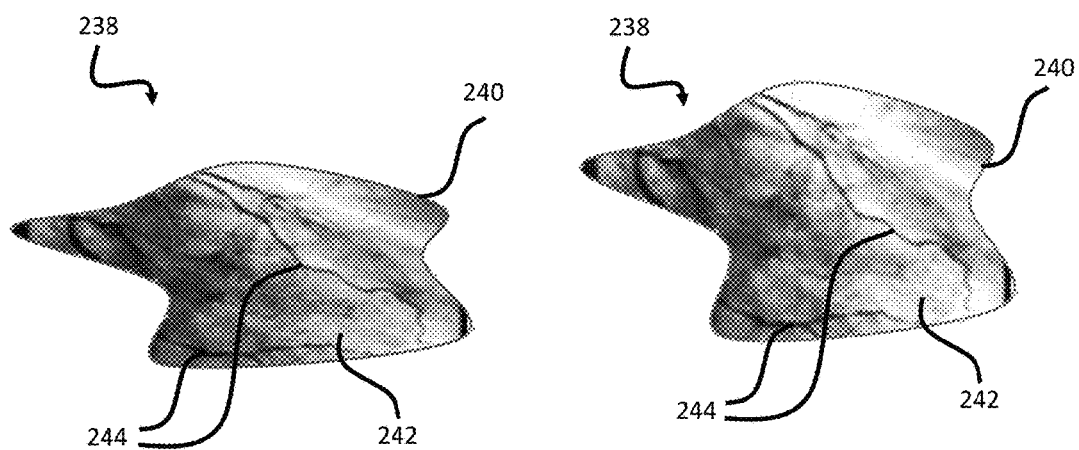
FIG. 13A illustrates a body's envelope and internal architecture.
FIG. 13B illustrates a distortion of the body's envelope and internal architecture.

Reference is now made to FIG. 13A showing for a body 238 its envelope 240 and its internal architecture 242 as typically seen in X-ray imaging. Two objects 244, in this case, blood vessels, are visible. In FIG. 13B, the same object, body 238, is shown, but it is distorted, as seen from the shape of its skin, envelope 240. The internal architecture of the body 238 in its distorted shape is calculated by rubber sheeting the internal architecture 242 of FIG. 13B. Rubber sheeting software is available in GIS and CAD systems such as the "Raster design" tool in the Autodesk CAD software available from AutoCad.

Figure 14:
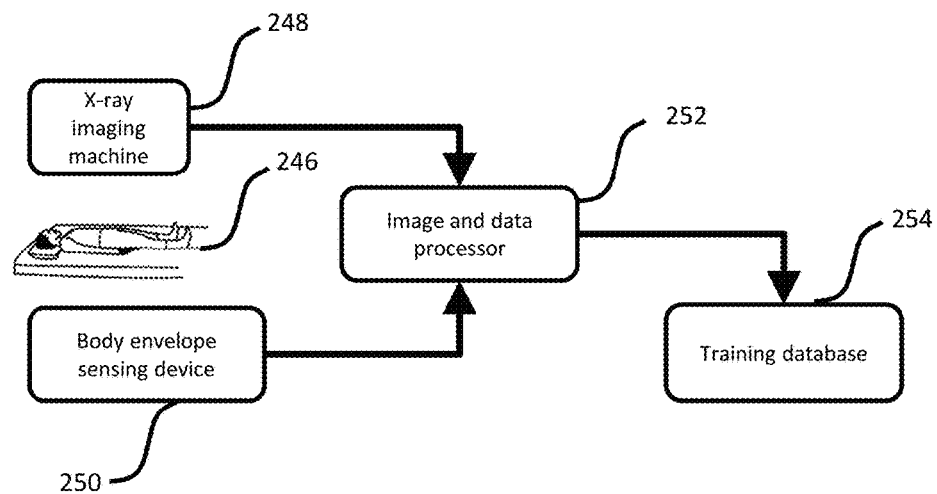
FIG. 14 illustrates the interaction of equipment and the functions they perform during a training session in accordance with an embodiment of the invention.

A training session is represented schematically in FIG. 14, where X-ray imaging and shape sensing clothing are used to create a database of body envelopes and corresponding internal architecture. The patient 246 lies on the surgery bed and does not move. An X-ray machine 248 generates a video record of the arena of the body for which the operation is planned. Contrasting fluid is injected to the blood vessels to enable the vessels to appear in the X-ray images. A shape sensing device 250 (represented as a box in the schematic of FIG. 14 for clarity), including for example a shirt with shape sensing fibers weaved thereto, provides envelope data, and a processor 252 records both the envelope data and the X-ray images into a database 254.

Figure 15:
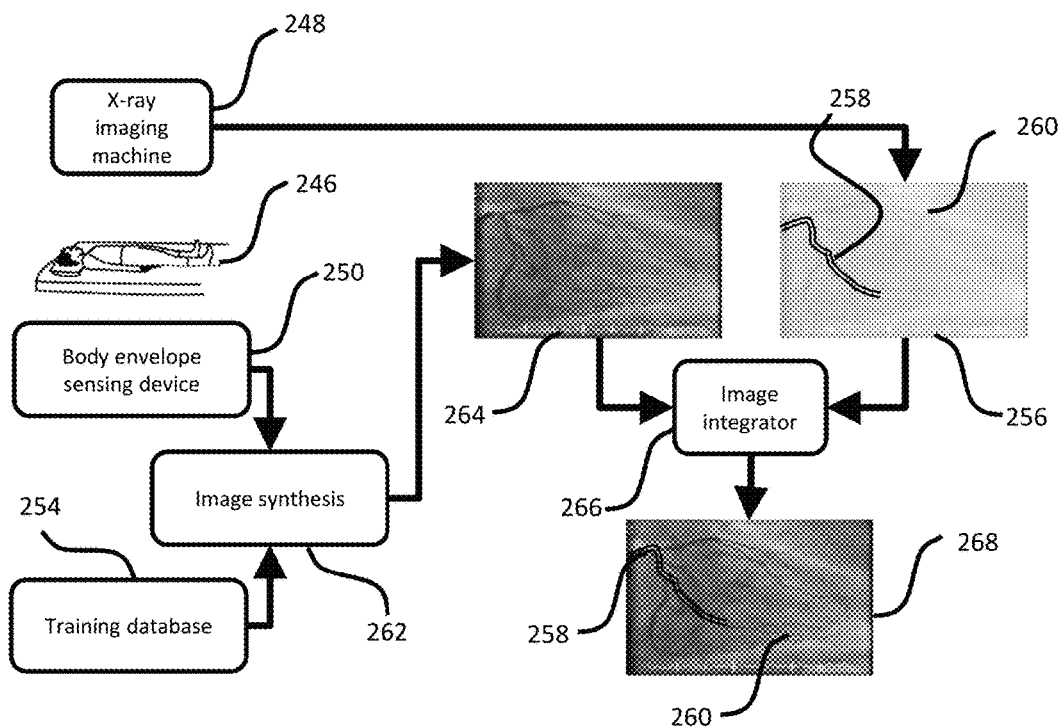
FIG. 15 illustrates the interaction of equipment and the functions they perform during a operation session in accordance with the embodiment of FIG. 14.

An operation session following the training session is represented schematically in FIG. 15. The patient 246 remains lying on the surgery bed in the same posture as was the state during the creation of the training database. The X-ray machine 248 images the patient's body this time using a very low dose of radiation. It is no longer necessary to see details of live tissue. Only enough radiation is needed to distinguish between the soft tissues of the body from the metallic catheter and thereby create an image 256 on which the catheter 258 is clearly seen while the background tissue 260 is not interpretable.

The body envelope sensing device 250 provided real time information about the envelope of the body, now stored in the database 254, and an image synthesizer 262 uses the body envelope data extracted from the training database 254 to synthesize the background image of the body using any of the methods described above. The synthetic image 264 does not include the catheter, as the image is synthetic and is not connected to the real time imager.

An image integrator 266 combines the synthetic image 264 with the X-ray image 265 to produce a full image 268 of the operation to be used by the surgeon, who is now able to see an image of the catheter 258 and tissue 260 using only low doses of radiation and contrasting fluid.

The image integrator 262 is configured to detect vessels that are very similar in shape and very close to the pattern of the catheter 258, and, when such correlation is detected, to rubber sheet the synthetic image so that the two will align under the assumption that the catheter must be travelling inside the vessel.

Figure 16:
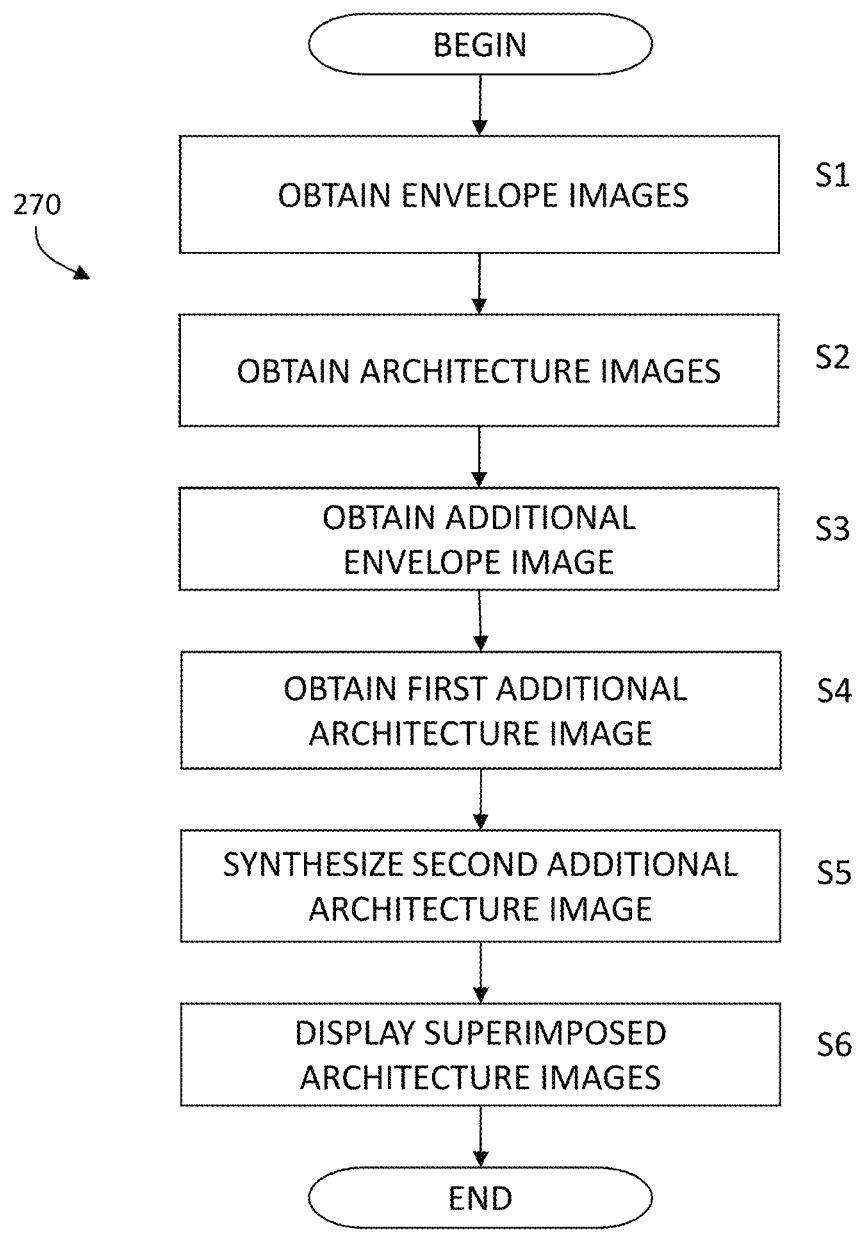
FIG. 16 presents a flowchart illustrating the invention embodied as a method of displaying a tool moving within a patient's body.

The present invention may also be embodied as a method of displaying a tool moving within a patient's body. Using this method, health care personnel directs a tool through the body while exposed to much less radiation than that of conventional counterpart methods, and the patient receives less contrasting fluid for the X-ray imaging that is performed. This method is described with reference to the flowchart 270 in FIG. 16.

The first steps occur during a first time period, the training session.

A first set of envelope images of a portion of the body is obtained. (Step S1.) The first set of envelope images provides data indicating the size and shape of the body portion. Non-limiting examples of such body portions include the hips and lower torso (as would be of interest for a colonoscopy) and the full torso (which may be of interest for angioplasty). The envelope images may be obtained using shape sensing fibers connected to a garment snugly fitting the body portion or alternatively using a three-dimensional scanner as discussed with respect to the embodiments described above.

A first set of architecture images of the body portion is obtained. (Step S2.) The first set of architecture images provides data indicating the locations of internal body parts. The first set of architecture images may be obtained using X-ray imaging.

The next steps occur during a second time period, the operation session.

An additional envelope image is obtained. (Step S3.) The additional envelope image also provides data indicating the size and shape of the body portion. The additional envelope image may also be obtained using shape sensing fibers connected to a garment snugly fitting the body portion or alternatively using a three-dimensional scanner.

A first additional architecture image is obtained. (Step S4.) The first additional architecture image indicates the location of the tool. The first additional architecture image may be obtained using X-ray imaging. The power used for the X-ray imaging may be lower than that used for obtaining the first set of architecture images, as it is not necessary that the X-ray data indicate the locations of the surrounding internal body parts.

Now, a second additional architecture image is synthesized using the first set of envelope images, the first set of architecture images, and the additional envelope image. (Step S5.) This second additional architecture image indicates the location of the surrounding internal body parts, which is why it is not necessary to use so much X-ray power in step S4. An image from the first set of envelope images is found that most nearly matches the additional envelope image. This architecture image matching the envelope image found may become the second additional architecture image, or it may be further processed according to the discussion above, if no image from the first set of envelope images was found sufficiently close to the additional envelop image.

The final step of this method is to display the first additional architecture image superimposed on the second additional architecture image (or vice versa) to show both the tool and the surrounding body parts. (Step S6.) Accordingly, a tool moving within a patient's body can be displayed using much less radiation and contrasting fluid for the X-ray imaging.

Figure 17A:
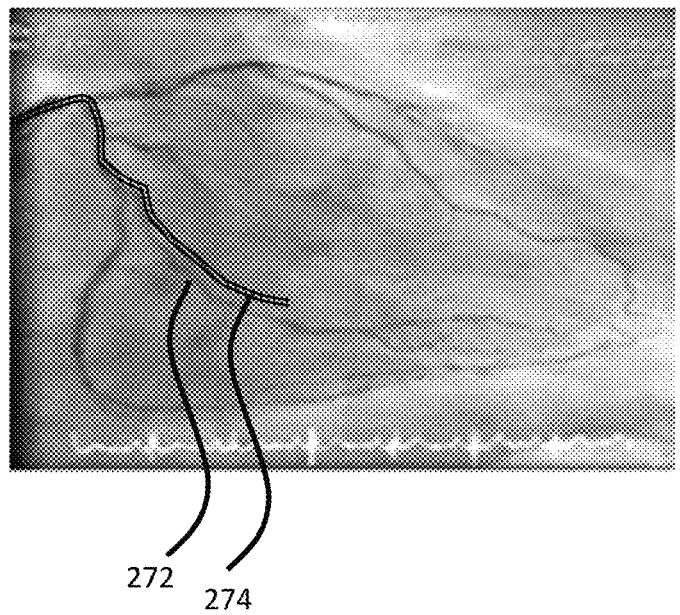
FIGS. 17A and 17B illustrate rubber sheeting applied to align an image of a tool with an image of a blood vessel when providing a superimposed image of both.
Figure 17B:
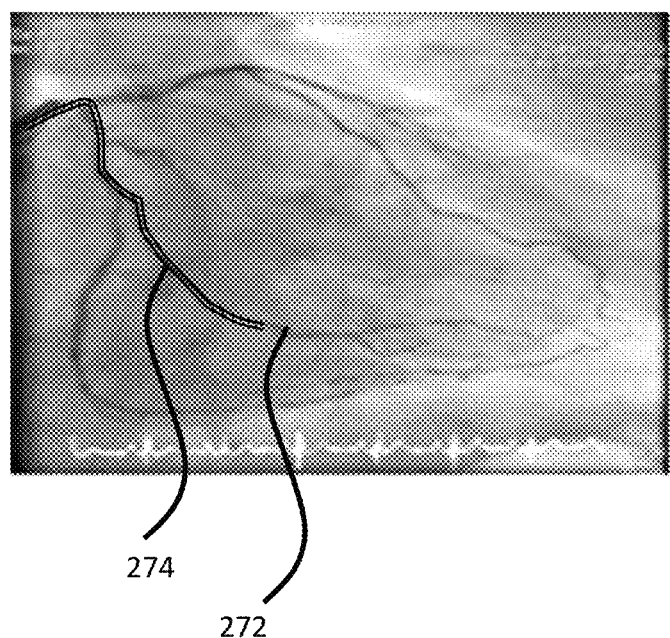

When superimposing the architectural images, rubber sheeting may be implemented. An example of the improvement that rubber sheeting provides is illustrated using FIGS. 17A and 17B. In FIG. 17A, before the rubber sheeting is applied, a vessel 272 evidently hosting a catheter 274 is displayed as if the catheter 274 were not within the vessel 272. After the rubber sheeting, the vessel 272 is shown hosting the catheter 274.

The present inventors further realized that fiber optic position and shape sensing, when implemented correctly, may be employed to facilitate head tracking. The need to track the position of a person's head in six degrees of freedom of motion is well known in the arts of neck treatment, computer games, automotive design, avionic control, and more. Methods for tracing head positions use video imaging and processing, accelerometers, inclinometers, and more.

Embodiments disclosed herein implement head tracking by tracing and measuring head motion relative to a subject's shoulders (as opposed to a fixed point space), by imposing negligible weight and inconvenience upon the head, by being visible to strangers in public areas so as not to cause embarrassment to the user, by being easily portable and usable almost everywhere without a significant external infrastructure (such as that employing cameras), by being accurate and fast, and by being immune to noises caused by the body motion. The embodiments can measure and trace the relative position of the head in all six degrees of freedom, pitch, roll, yaw, and the three Cartesian (X, Y, and Z) degrees.

Embodiments of the invention take many forms.

In one embodiment, shape sensing fibers are weaved into a flexible collar that the user wears on his/her neck, while an interrogator is held in a pocket of the user's shirt or coat.

In another embodiment, the fibers are weaved into a vertical flexible strip, whose top side is held against the skull of the user by a hat, and its bottom side is fixed to the back of the user by a band or by a tape.

In an additional embodiment, the fibers are embedded into one or more earphone cables, while the earphones are held in the users' ears, and the bottom of the fibers is fixed to the back of the user.

In still another embodiment, the earphones are functional and are connected to an audio source, such as a radio, so that the user can hear music or alerts regarding the wrong position of the neck or shoulders while wearing the device.

In yet another embodiment, the fibers are embedded into one eyeglass neck strap, while the ends of the fibers are fixed to the back of the user.

In another embodiment, the system also has fibers embedded in a back of a shirt, tracing the shape of the back while simultaneously tracing the position of the head.

Figure 18:
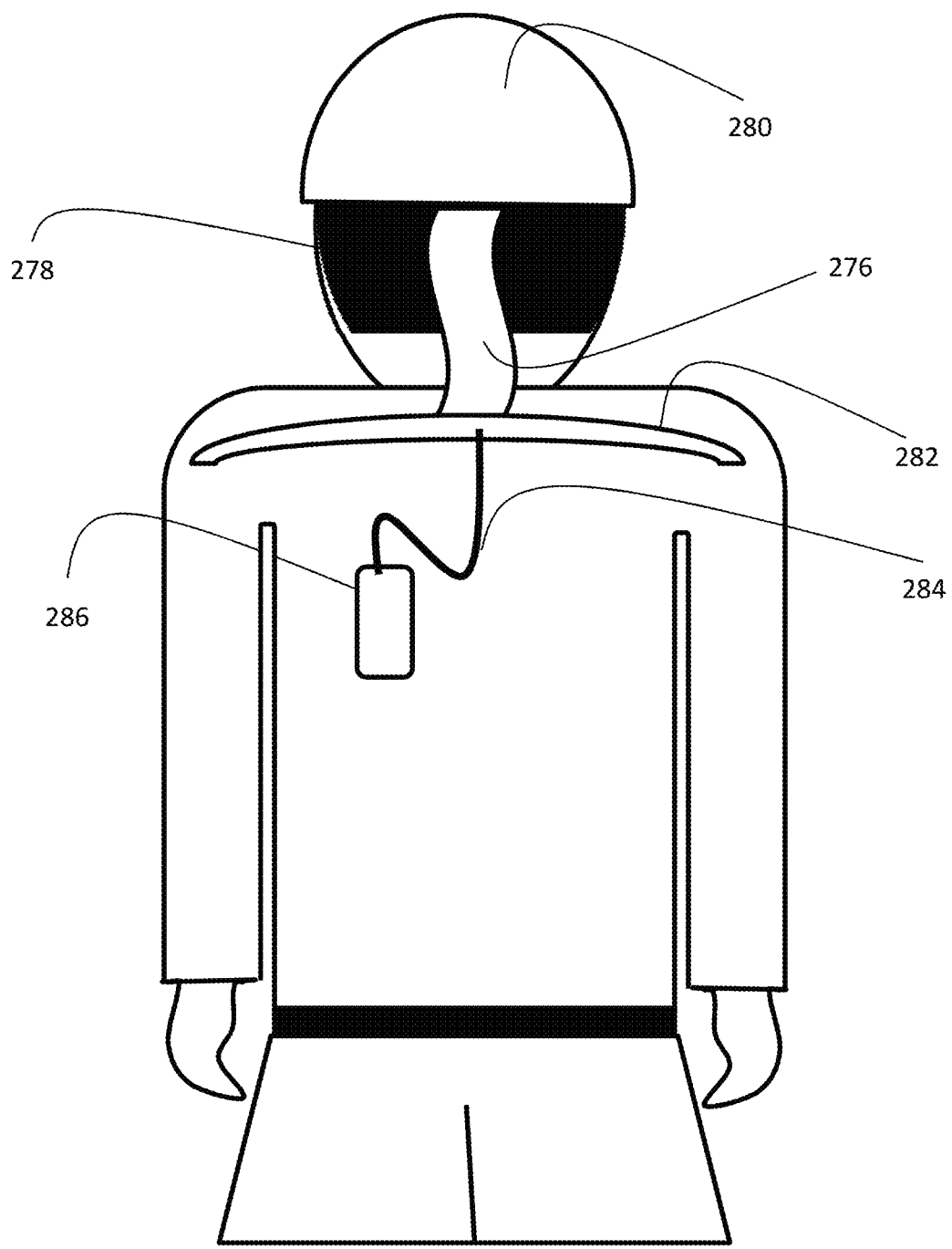
FIG. 18 shows a rear view of a user wearing an embodiment of the invention that monitors head movement.

FIG. 18 shows a rear view of a user wearing a head-tracing strip 276, for example, a strip formed of fabric. The top side of the strip is held in place on the head 278 by wearing an ordinary hat 280 over it. The bottom side of the strip 276 is attached to the upper back of the user by strip of medical sticky tape 282 or by being attached to an undershirt that the user wears under his/her clothes. Shape sensing fibers (not illustrated for clarity) are weaved into the strip 276 so that any motion of the top of the strip 276 relative to the bottom of the strip 276 is captured and traced. The fibers are connected 284 to a small interrogator 286 that can be held in a pocket of the user or on a belt under the clothes (not shown). The strip 276 can be covered by a fabric sleeve that has a similar color to the user's hair, so that the strip 276 minimally detracts from the appearance of the user. When the user moves his/her head, the strip 276 flexes and its shape is traced, giving a precise six-dimensional tracking of the motion of the head 278 over the shoulders.

Figure 19:
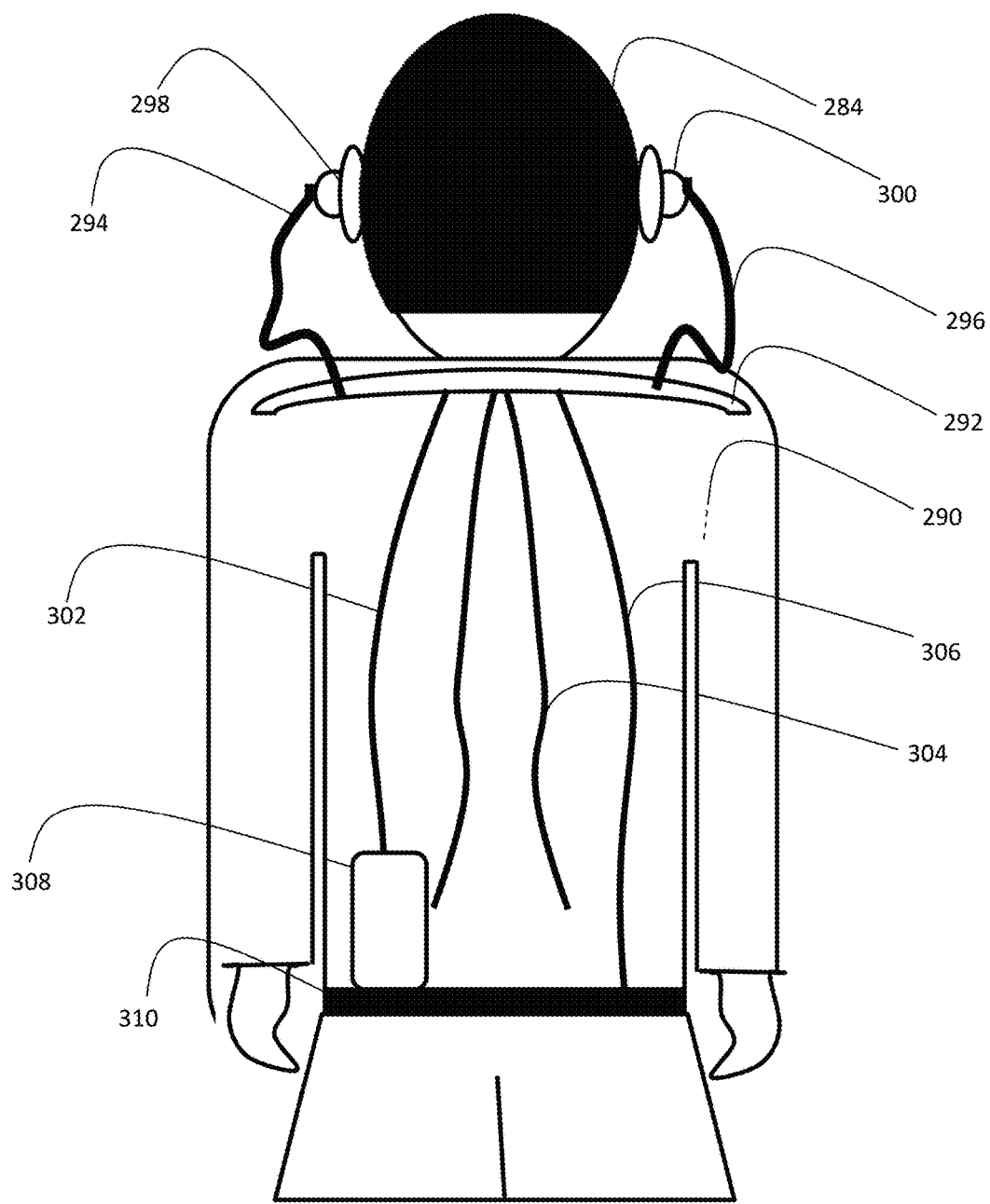
FIG. 19 shows a rear view of a user wearing another embodiment of the invention that monitors head movement.

FIG. 19 shows a rear view of another embodiment, in which the user 288 is wearing an undershirt 290 that has a support strip 292 made of a slightly tough material between the shoulders. Two earphones wires 294 and 296 come out of the strip 292 behind the user's ears. The earphones 298, 300 are plugged into the user's ears. The flexible wires of the earphones comprise, in addition to the audio cable, a shape sensing fiber. By tracing the shape of the wires all the way from the shoulder support strip 292 to the earphones 298, 300, the fibers provide a real-time accurate indication of the location of the ears relative to the shoulders.

Additional shape sensing fibers 302, 304, and 306, or a continuation of the fibers mentioned above, are woven into the undershirt 290 along the back. These fibers 302, 304, and 306 provide additional information on the shape of the user's back, which is useful for diagnosing scoliosis and in monitoring rehabilitation.

The information is recorded in a small electronic interrogator 308 that can be attached to the user's belt 310. In the interrogator 310 or near it there may be a source of audio content, such as a radio receiver or an MP3 player, and the content is played to the user via these earphones. Therefore, it is not apparent to the public that the user is undergoing treatment or observation.

Figure 20A:
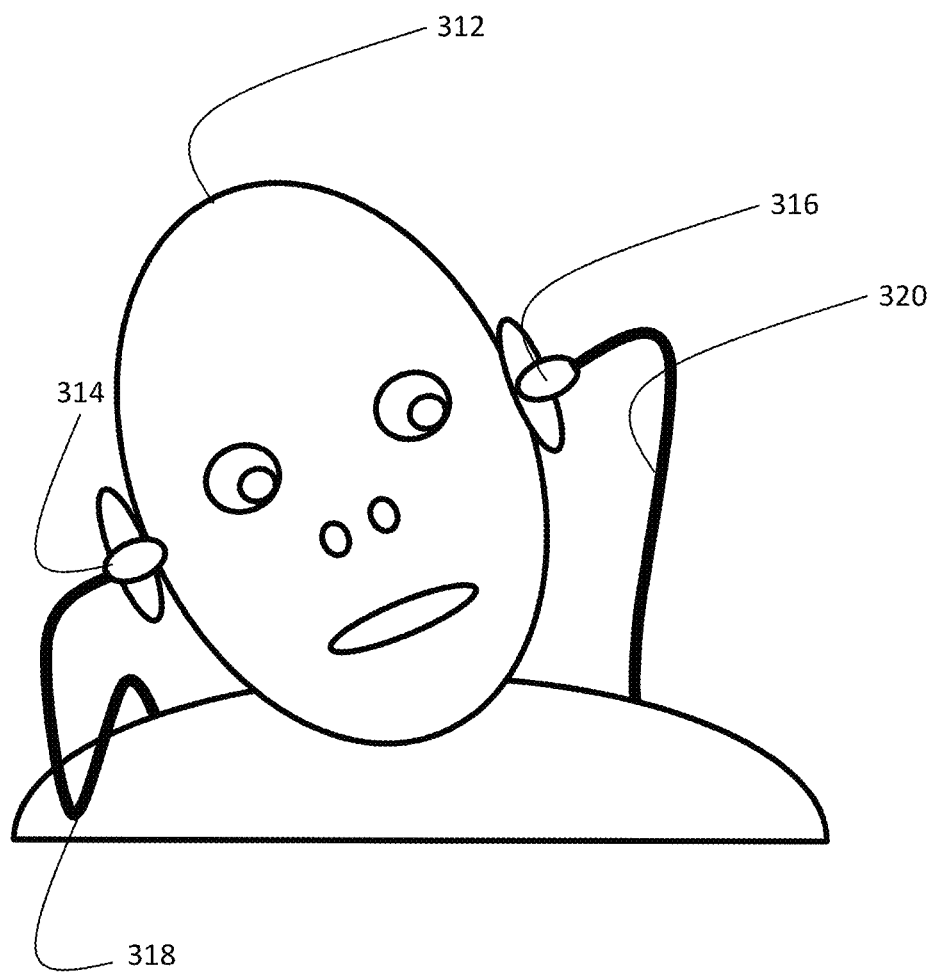
FIG. 20A shows a tilted head with earphones.

FIG. 20A shows a user 312 with tracing-enabled earphones 314 and 316 plugged into his ears, and cables 318, 320 comprising shape sensing fibers connected to fixed points on his shoulders or back, as described in FIG. 19 above. The shape sensing fibers provide information about their shape, including the coordinates of their ends at the tracing-enabled earphones 314 and 316 that are located inside the external ear of the user.

FIG. 4B show an imaginary segment 320 extending between the two ends 322, 324 of the earphone wires 326, 328. This segment represents the orientation of the head in the coordinate system of the user's back, as the bottom ends of the wires 330, 332 are attached to the upper back.

The relative orientation of the segment 320 is a full indication of the relative orientation of the head, as the only degree of freedom of rolling around this segment is not relevant due to the structure of the body and neck.

Figure 20B:
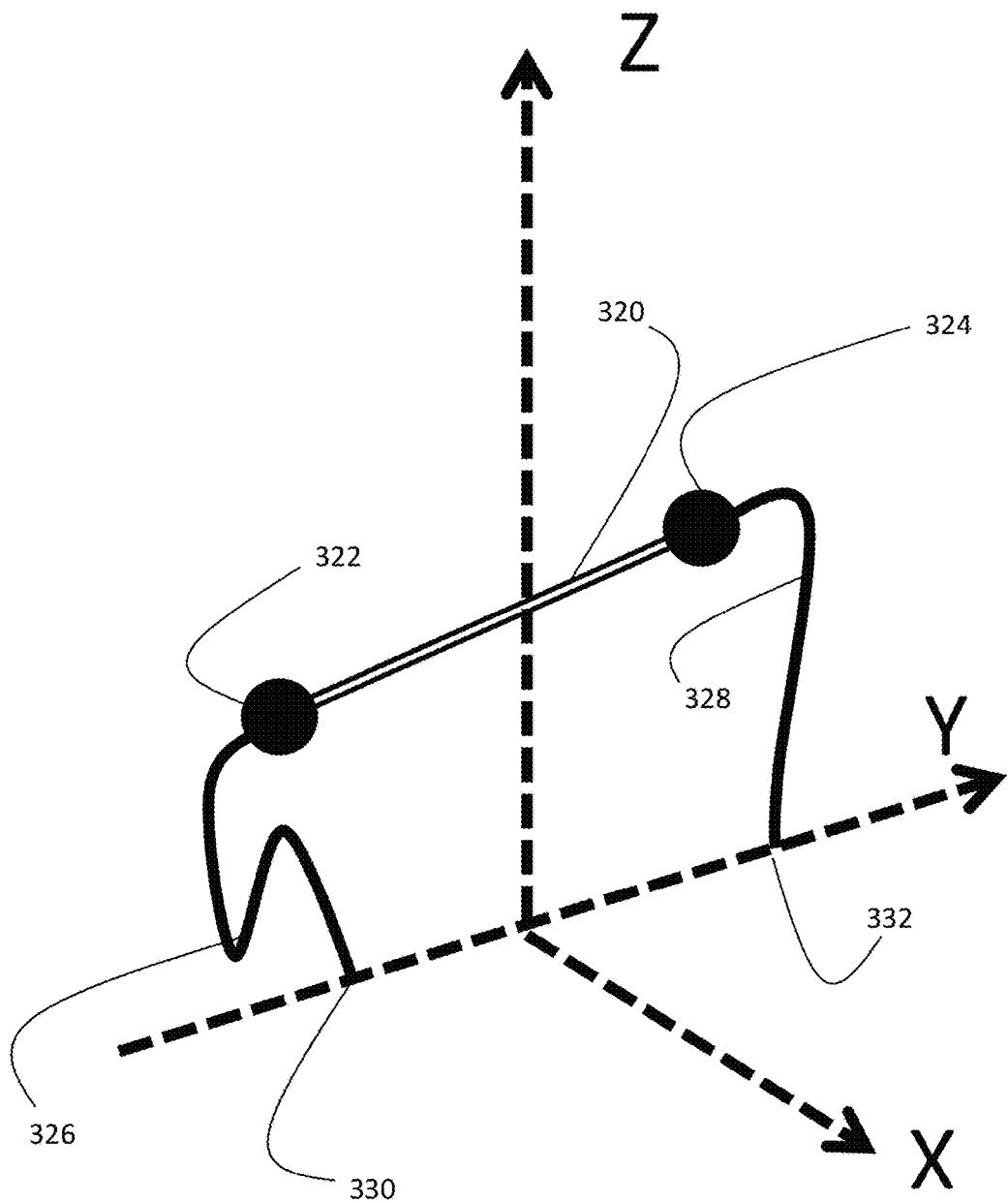
FIG. 20B shows the geometry of the tilting of FIG. 20A.
Figure 21:
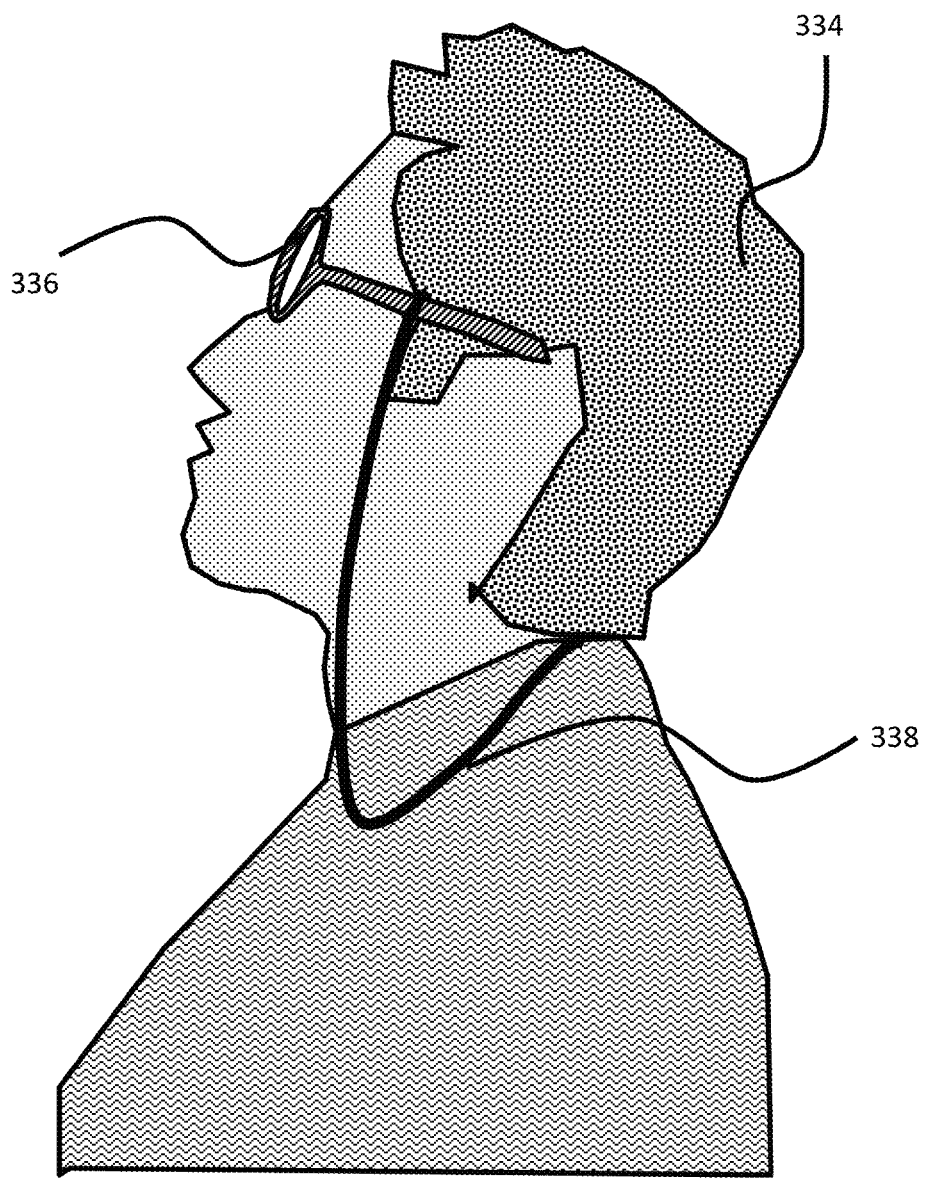
FIG. 21 shows fiber optic shape sensing fibers aligned with a neck strap for eyeglasses.

FIG. 21 shows a user 334 wearing a pair of eyeglasses 336 and a neck strap 338 tied to both temples of the eyeglasses 336 and extending to behind the neck to the back of the user 334. Embedded within the neck strap 338 is at least one shape sensing fiber (not shown) that goes to an interrogator (not shown). By tracing the shape of the straps, an interrogator can position the ends of the strap in space relative to the user's back and determine the motion of the head in a very similar way to the way described with respect to the embodiments of FIGS. 20A and 20B.

Accordingly, some embodiments of the present invention may be regarded as a device for tracing motion of a first object relative to a second object, where the first object may be a person's head and the object may be person's back. The device has at least two shape sensing fiber. One first shape sensing fiber mechanically links to the first object at a first point, and a second shape sensing fiber mechanically links the first object at a second point spaced apart from the first point. Even if the first and second points are on eyeglasses worn by the user, they are still mechanically-linked to the head (though the eyeglasses). The two shape sensing fibers are configured for mechanical linkage to the second object, either directly or through an interrogator.

Having thus described exemplary embodiments of the invention, it will be apparent that various alterations, modifications, and improvements will readily occur to those skilled in the art. Alternations, modifications, and improvements of the disclosed invention, although not expressly described above, are nonetheless intended and implied to be within spirit and scope of the invention. Accordingly, the foregoing discussion is intended to be illustrative only; the invention is limited and defined only by the following claims and equivalents thereto.

What is claimed is:

1. A system comprising a garment and a controller;
   wherein, the garment comprises clothing stretched over part of a wearer's body and a plurality of optical fibers connected to fabric of the garment to enable fiber optic position and shape sensing; and
   wherein, the plurality of optical fibers comprise a plurality of fiber Bragg gratings;
   the system characterized in that:
   a) at least some of the optical fibers cross each other and press on each other, thus creating pairs of points of stress at different lengths along the respective fibers, but with identical XYZ coordinates in a reference frame relative to the body of the wearer; and
   b) the controller is configured to:
      i) interrogate the optical fibers at sampling rates of hundreds of times per second enabling the position of each fiber Bragg grating along the optical fibers to be determined to provide a record of the motion of the part of the wearer's body enclosed by the clothing;
      ii) use the points at which the optical fibers cross each other for calibration of the sensed positions of the fibers, forcing the positions of said points to be the same in the reference frame relative to body of the wearer, and interpolating between said points to calibrate other points along the fibers; and
      iii) at least some of the optical fibers extend along at least four sides of the part of the wearer's body enclosed by the clothing, to monitor general cross sections along the part of the body.

2. The system of claim 1, wherein the fabric of the garment is sized and shaped to envelop at least a portion of a wearer's body below the waist.

3. The system of claim 1, wherein the fabric of the garment envelops at least a portion of the wearer's body below the waist, and wherein the shape of the portion of the optical fiber conforms to the enveloped portion of the wearer's body.

4. The system of claim 1 further comprising a switch enabling successive interrogation of the optical fibers.

5. A method of monitoring gait of a subject, the method comprising:
   providing the subject with the garment of claim 1;
   interrogating the optical fibers to obtain coordinates along the optical fibers; and
   repeating the interrogating to obtain coordinates along the optical fibers at multiple instants in time.

6. The method of claim 5, wherein, for a set of points along the optical fibers that for at least one instant in time lie in a plane parallel to the subject's waist and intersecting the subject's legs, the interrogating is repeated to find the coordinates of the set of points at multiple instants in time to monitor changes in the cross sections of the subject's legs.

7. The system of claim 1, wherein the fabric of the garment is sized and shaped to envelope at least a portion of at least one of a wearer's legs, and at least one of the optical fibers extends down and up the at least one leg at least two times.

8. The system of claim 7, wherein the at least one optical fiber extends in a path along the at least one leg in front, in back, on the inner side, and on the outer side.

9. The system of claim 8, wherein the at least one optical fiber curves in the form of a U-turn at an end of the garment.

10. The system of claim 1, wherein the garment comprises one of: a pair of trousers, a shirt, and a sock.

* * * * *